United States Patent [19]

Keene

[11] Patent Number: 5,325,294
[45] Date of Patent: Jun. 28, 1994

[54] MEDICAL PRIVACY SYSTEM

[76] Inventor: Sharon A. Keene, 230 Penobscot St., Rumford, Me. 04276

[21] Appl. No.: 907,741

[22] Filed: Jun. 29, 1992

[51] Int. Cl.$^5$ .............................................. G06F 15/00
[52] U.S. Cl. ................................ 364/413.01; 379/95; 340/825.34
[58] Field of Search ............... 364/413.01, 401; 380/4, 380/25; 379/95; 235/380; 340/825.31, 825.32, 825.34, 825.36; 395/725, 425

[56] References Cited

U.S. PATENT DOCUMENTS

| | | | |
|---|---|---|---|
| 3,872,448 | 3/1975 | Mitchell, Jr. | 340/172.5 |
| 4,835,372 | 5/1989 | Gombrich et al. | 235/375 |
| 4,858,121 | 8/1989 | Barber et al. | 364/406 |
| 4,876,717 | 10/1989 | Barron et al. | 380/25 |
| 5,065,315 | 11/1991 | Garcia | 364/413.01 |
| 5,241,594 | 8/1993 | Kung | 380/4 |

*Primary Examiner*—Roy N. Envall, Jr.
*Assistant Examiner*—Laura Brutman

[57] ABSTRACT

Method and apparatus for providing authorized access to medical information concerning an individual while preserving the confidentiality of, and preventing unauthorized access to, such information. A computer database receives and stores the individual's medical information, after the individual is tested to establish this information and the date on which such information was most recently obtained. The computer database does not contain the individual's name, address or any other similar information by which the individual can be identified. The individual is given an identification card containing a photograph or holographic image of the individual and containing a confidential first identification number that is unique for the individual, where both the image and the first identification number are visually perceptible and cannot be altered on the card without detection of such alteration. The individual is also given a confidential second identification number that is not contained on the card and need not be unique for that individual. The computer database can be accessed telephonically, and the individual's medical information, or a portion thereof, can be read only by an inquiror, if the inquiror or the individual first provides the individual's first and second identification numbers. The inquiror can use the image and first identification number on the individual's card to confirm the identity of that individual but need not be told the individual's second identification number. After inquiror establishes the identity of the individual, the inquiror, with the assistance of the individual, can obtain a telephonic readout of the individual's medical information.

11 Claims, 1 Drawing Sheet

MEDICAL PRIVACY SYSTEM

FIELD OF THE INVENTION

This invention relates to a computer database system that maintains certain medical test information and preserves the confidentiality of the test information and the identity of the patient, by restricting access to the test information to selected persons.

BACKGROUND OF THE INVENTION

Medical test information for a patient is normally kept confidential, and is often available only with prior written approval by the patient. In some instances, a person other than the patient may have a need to know, or even a right to know, certain medical test information on the patient, and may need to be able to verify the accuracy of this information by consulting an unbiased source of such information. At one end of the spectrum, this medical test information could include the patient's blood type, serious allergies, and chemicals or medicines known to produce disagreeable reactions in the patient. At the other end of the spectrum, the medical test information could consist of a yes/no answer to a single question, such as whether the most recent medical test of the patient indicates that the patient tested positive, or negative, on a sero-test for the presence of the human immunodeficiency virus ("HIV") or some other sexually transmittable disease ("STD").

A confidential information system for identifying and locating persons who are compatible (a matchmaking system) is disclosed by Shapira in U.S. Pat. No. 5,086,394. Each "candidate" carries a memory device having a transceiver, with the memory device containing a list of personal characteristics, such as personal traits and interests. A local processing unit receives this information from each candidate who is available locally, compares the data received to find compatible persons of opposite gender, and automatically pages the candidates for whom one or more matches is found. An introduction of the matched candidates is then arranged by a telephone call or other communication means that matches their candidate codes. No information, other than the fact that a possible match has been found, the name and address of the other candidate and place and time for a possible meeting, is provided to each candidate.

What is needed is a system for providing controllable access to medical information on a given person where: (1) such access allows the inquiror or requestor, with the approval of the given person, to verify that the identity of the person for which such information is being sought; (2) authorized access to such medical information is controlled by the given person; and (3) unauthorized access to the system will not enable a trespasser to identify whose medical information is being accessed. Preferably, the requestor or inquiror, with the approval of the given person, should be able to obtain the test information, to certify the accuracy of this information, and to determine how current is this information, reasonably promptly, without a formal and time-consuming submission of a written request to a medical provider. Preferably, the system that provides such medical test information, in response to a pre-approved request by the requestor, should preserve the identity of the patient in confidence.

SUMMARY OF THE INVENTION

These needs are met by the invention, which in one embodiment provides a computer database containing the relevant medical test information for each person who is a "member" of the system. Access to this test information, or to selected parts of such information, is available only by provision of an Account No. or member's identification ("ID") No., which is indelibly imprinted on an ID card carried by the member, and provision of a personal identification number ("PIN") that is selected by and known only to the member, and is not carried on the ID card. The ID card also contains a photographic or holographic image of the member for photo identification purposes, and neither the Account No. nor the image can be altered.

The member contacts the system database using a touchtone telephone and enters the Account No. and the PIN to obtain access to the member's medical test information. The member then hands the telephone to a partner or other designated person who has a "need to know" such information. Using voice mail communication, the system first verbally confirms the Account No., then verbally announces the medical test information to be communicated to the designated person. The recipient of this information has temporary possession of the member's ID card and confirms the member's identity, using the image of the member and the member's Account No. contained on the ID card. Optionally, the system can also: (1) include the date of the member's most recent medical test and notify the member and/or the partner if the medical test information is "stale" and needs to be updated; and (2) keep track of the number of times the database has been queried by the member within some selected time period (e.g., the preceding two months) and notify the member and/or the partner if the number of such queries exceeds a selected threshold number (e.g., five).

DETAILED DESCRIPTION OF THE INVENTION

Figure 1:
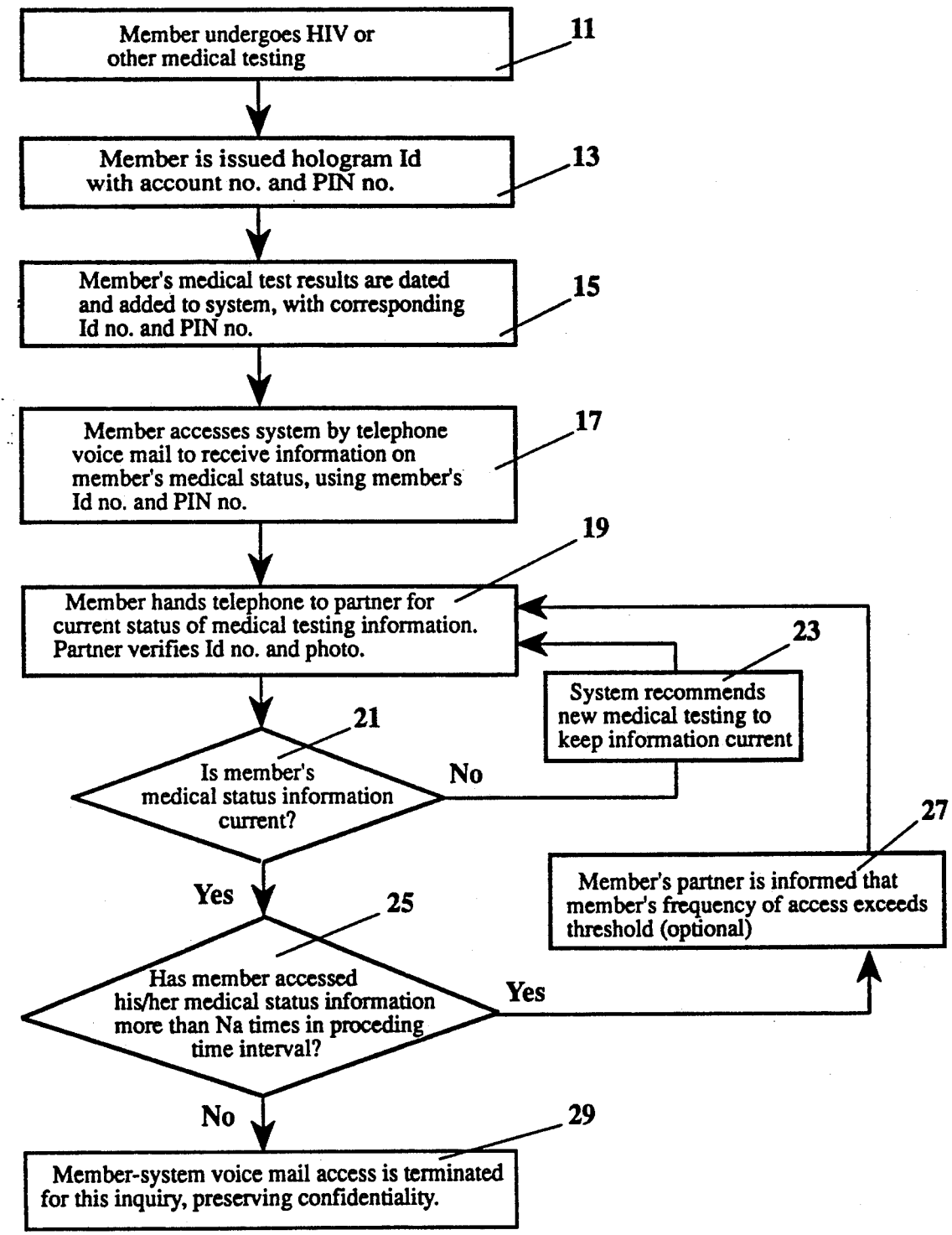
FIG. 1 is a flow diagram illustrating operation of the invention in one embodiment.

FIG. 1 is a flow diagram illustrating one embodiment of the invention and its operation. In step 11, a member undergoes testing for presence of the HIV virus (sero-testing) or medical testing for the presence or absence of one or more other conditions. In step 13, the member is issued a non-changeable holographic or photographic photocard with an indelible Account No. or other ID No. imprinted on the card. This card may have the size of a credit card. The card's primary purpose is to allow the member's partner to verify, through comparison of the member's image on the card with the member's face, that the Account No. imprinted on the card is correct. In step 15, the member's most recent medical test results are entered into the system database, together with the member's Account No. and a PIN that is selected by and known only to the member. The member must supply both the Account No. from the card and the member's confidential PIN in order to access the member's medical test information in the system. The member's name and address are contained in a second database that, preferably, must be accessed manually by provision of both Account No. and PIN; no computer can access this second database. This promotes and strengthens confidentiality of the fact that a given person is a member of the system and of a member's medical test information, by severing any deducible connection between this medical test information and the name or address of the corresponding member. The order of steps 11 and 13 may be reversed.

Assume that a member, whose medical test information is contained in the (first) system database, wishes to allow disclosure of this information to another person, such as a sexual partner. In step 17, the member accesses the system database by touchtone telephone. After a connection is initially established, the member enters the Account No. on the member's card and the member's confidential PIN, again using the touchtone telephone. The system optionally delays a response for a suitable time interval, such as $\Delta t_d \approx 10$ seconds, so that the member can hand the telephone to the member's partner or other person with a need to know this information (step 19). The system then uses voice mail or a similar verbal communication means to (1) verbally confirm the member's Account No., and (2) verbally inform the member's partner of the relevant medical test information stored in the system database.

If the member's medical test information is not sufficiently current (step 21), i.e., if the most recent medical test information is older than a selected time period, such as $\Delta t_c$=three months, the system may optionally inform the member or the member's partner of this circumstance and recommend retesting (optional) when the member accesses the system database (step 23). Alternatively, the system may prepare a notice, to be mailed to the member, that the member's medical test information is not sufficiently current and that the associated medical test(s) should be performed again on the member.

The system also monitors the number of times n that a member has accessed the system within a preceding time interval, such as $\Delta t_a$=two months. If the number of access events n is larger than a selected threshold access number $N_a$ (step 25), the system will optionally notify the member's partner that the threshold number $N_a$ of accesses has been exceeded (step 27), in order to advise the member's partner that the member's account has been fairly active during the immediately preceding time interval of length $\Delta t_a$. After the member's partner has been advised of the member's medical test information contained in the system database, and of any optional information contained therein, the member's voice mail access to the system database for this query is terminated (step 29).

Each individual member will be issued a photo identification and account number card prior to medical testing for an STD (e.g., HIV sero-testing or testing for gonorrhea, syphilis or herpes). A member is referred to an agreed-upon testing facility where the member's identity will first be verified, using a databank ID card, prior to obtaining a serum specimen. Results are reported according to account number; names are held in a separate non-accessible databank. Medical testing is performed by pre-existing facilities according to approved standards. Responsibility for informing a patient (the member being tested) of the results rests with the facility, as does medical follow-up for any patients whose condition is a concern to the medical provider. With the consent of databank members, official results will then be provided to the databank. Members have access to their individual account via telephone. Additional security is insured by provision of the PIN, which must be provided to access any account information. Once the account has been accessed, using the account number and PIN for verification, the most recent data of testing and current medical status of the member, along with his or her account number, will be reported by electronic voice. A brief delay is optionally programmed into the report to allow the member adequate time to hand the telephone to the member's partner. This method insures that only individuals selected by the member will hear this report. The member's partner will need to compare the account number reported with the member's identification card to confirm that the information pertains to that member; a member's name will not be included in the report. This helps maintain the confidentiality of the data. A 1-800 number may be provided to allow a member to access this information from anywhere within the United States and at any hour of the day or night.

Members will be required to update their medical status periodically, for example, at least once every six months, in order to maintain an active account. Any account that receives frequent use (which indicates the possibility of multiple partners) will require updated medical testing at shorter time intervals (e.g., every three months) to keep the account active. "Frequent" access may be defined as greater than five accesses (or any other selected number $N_a$ of accesses) per quarter. Once an account has reached this frequency, the data report will optionally include a warning to indicate the account has exceeded the selected frequency limit, and an updated medical test will be advised. If the member allows his/her account to deactivate, through failure to retest, the member is required to reactivate the membership and to provide proof of current medical status to reopen the account.

A member may be reminded of the limitations of present testing methods to detect the presence of infections addressed by the medical testing, due to the lag time in appearance of medically detectable symptoms after exposure to a disease.

A centralized computer databank is provided containing the account number and medical status of present members of the system, accessible to members by coded telephone access. Access to account information requires a PIN code to help maintain the security of access. The system provides automatic deactivation of any account that has not been updated according to the previously described criteria. Each report includes the date of the last relevant medical test.

Local offices may be provided for examining personal identification for proposed members, as well as taking photos, and distributing ID card and PIN numbers. Results may be keyed in by local offices, or may be entered directly by the official testing facility.

For each member, a non-defaceable, non-reproducible identification card is provided, resembling a credit card and utilizing a hologram marking tag or photo image to inhibit tampering. The card will also incorporate information found on most drivers' licenses to provide reliable identification of the member. The account number provided for each card is a combination of letters and numbers for easier comparison to and verification by numerical account number.

A member need not share this information with his or her employer, co-worker, insurance company, or neighbor. However, one person has a right to know of a member's STD status, the member's sexual partner. Each sexually active individual has an important interest in knowing the STD status of that individual's partner, given the dire consequences of inadvertently picking up the virus or transmitting it. This is especially important, given the high failure rate of condoms, their known propensity to break, slip and fail to prevent pregnancy or prevent transmission of certain STD viruses. Furthermore, each individual has a right to decide if an emotional commitment is to be made, or if the risk of STD infection by becoming sexually involved with a sero-positive partner is to be accepted. It is also incumbent on heterosexual partners to avoid procreation if one of the partners tests positive for an STD, given the risk of transmission of this disease to the fetus.

Studies reported in 1989 indicated that a majority of the public at that time was supportive of "mandatory" testing for everyone. Two objections raised were invasion of an individual's privacy and possible discrimination. This approach offers a means for confidentially relaying a person's STD status to other persons who are most affected—sexual partners of that person. Concern about discrimination in the workplace and for insurance purposes can be met by this approach. Informed consent and minimization of the risk of transmission of STD infection are the primary concerns. At present, the public feels helpless to control or reduce the risk. This approach encourages members to take note of their own sexual practices and high risk behavior by requiring more frequent testing of individuals who apparently have multiple partners in a given time interval. The emphasis is on modification of a member's own sexual practices, revealing the member's own behavior as a contributing factor to the associated risk. This approach allays concerns about known sero-positive people failing to disclose their condition.

Member confidentiality is controlled by excluding members' names from the databank. If an invasion of the databank occurs, it would be impossible to make any identification of personal members. The only files containing both the member's name and account number together will be accessible only manually, not through this system.

The issue of limitations of the serum test becomes an advantage of proportional hazard. Because condoms have been shown not to be fully effective in providing lifetime protection against sexually transmittable diseases, it is important to know the medical status of one's partner. Although a negative result does not exclude the presence of infection if a member has been recently infected, a negative result will usually indicate lack of infection. In a high risk situation, combining barrier protection with frequent medical testing should decrease the risk of transmission of infection. As more individuals become members and use the system, and as the size of the medically tested population increases, the actual incidence and risks can be more accurately determined.

I claim:

1. A method for providing authorized access to medical information concerning an individual while preserving confidentiality of, and preventing unauthorized access to, such information, the method comprising the steps of:

storing the individual's medical information, but not the individual's name or address, in a computer database;

providing the individual with an identification card containing a visually perceptible image of the individual and containing a visually perceptible confidential first identification number for the individual, the image and the first identification number being unalterable on the card;

providing the individual with a confidential second identification number that is not contained on the card; and providing telephonic access to the computer database, and allowing any inquiror to obtain a verbal readout of the individual's medical information, or a selected portion thereof, if the inquiror or the individual first provides the individual's first and second identification numbers, the readout of the individual's medical information also indicating the number N of times this medical information has been read out in a selected time interval including the time of the present readout.

2. The method of claim 1, further comprising the step of indicating the most recent date of testing on which said individual's medical information is based, as part of said readout.

3. The method of claim 2, further comprising the steps of:

determining said most recent date of testing and the number D of days that have passed since said most recent date of testing; and if the number D exceeds a selected number $D_M$, advising said individual, as part of said readout, that said individual must be retested to establish a new most recent date of testing before said individual's medical information may be subsequently read out from said database.

4. The method of claim 3, further comprising the steps of:

comparing said number N with a selected positive number $N_M$; and if said number N is larger than the number $N_M$, reducing said number of days $D_M$ to a selected smaller number of days $D_L$.

5. The method of claim 1, wherein said first identification number is unique for that individual.

6. The method of claim 1, further comprising the step of providing said individual's birth date on said identification card.

7. The method of claim 1, further comprising the step of providing on said individual's identification card a telephone number to establish said telephonic access with said database.

8. The method of claim 1, further comprising the steps of:

storing said individual's name and address at a location separate from said medical information for said individual; and allowing access to the name and address of said individual only upon presentation of at least one of said first identification number and said second identification number.

9. The method of claim 8, further comprising the step of requiring presentation of said second identification number for access to said name and address information for said individual.

10. The method of claim 1, further comprising the step of providing a photographic image of said individual as said visually perceptible image.

11. The method of claim 1, further comprising the step of providing a holographic image of said individual as said visually perceptible image.

* * * * *